United States Patent
Sekiguchi et al.

[11] Patent Number: 6,136,881
[45] Date of Patent: Oct. 24, 2000

[54] PHOTOCURING RESIN COMPOSITION FOR ORTHODONTICS

[75] Inventors: Toshihiro Sekiguchi, Tokyo; Shunji Sugano, Ishikawa-ken, both of Japan

[73] Assignee: GC Corporation, Tokyo, Japan

[21] Appl. No.: 09/146,164

[22] Filed: Sep. 3, 1998

[30] Foreign Application Priority Data

Sep. 10, 1997 [JP] Japan ................................. 9-261161

[51] Int. Cl.⁷ .............................. C08K 3/36; C08K 5/205; A61C 5/00; C08L 75/04; C08L 75/16

[52] U.S. Cl. ............................. 522/83; 522/81; 522/96; 522/908; 433/222.1; 433/228.1

[58] Field of Search ............................. 522/96, 173, 174, 522/908, 81, 83; 433/222.1, 228.1

[56] References Cited

U.S. PATENT DOCUMENTS

| | | | |
|---|---|---|---|
| 4,711,913 | 12/1987 | Tateosian et al. | 522/14 |
| 5,317,074 | 5/1994 | Hammar et al. | 528/44 |
| 5,502,087 | 3/1996 | Tateosian et al. | 523/115 |

*Primary Examiner*—Susan W. Berman
*Attorney, Agent, or Firm*—Oblon, Spivak, McClelland, Maier & Neustadt, P.C.

[57] ABSTRACT

A photocuring resin composition for orthodontics is disclosed, comprising:

(a) 5~50% by weight of a urethane bond-free (meth) acrylate having an average molecular weight of 100~300 and having at least one unsaturated double bond;

(b) 10~60% by weight of a urethane bond-containing (meth)acrylate having an average molecular weight of 300~5,000 and having at least one unsaturated double bond;

(c) 5~30% by weight of a crosslinked polyurethane powder;

(d) 10~50% by weight of an inorganic filler; and (e) 0.03~3% by weight of a photocuring initiator.

By using the resin composition for orthodontics of the invention, not only an orthodontic appliance with a good precision can be directly prepared in the oral cavity of a patient within a short period of time without using a gnathostatic model, but also the resulting orthodontic appliance has a proper elasticity so that a thorough retention strength can be obtained by only utilizing a tooth undercut without imparting a retention structure such as a clasp.

1 Claim, No Drawings

# PHOTOCURING RESIN COMPOSITION FOR ORTHODONTICS

FIELD OF THE INVENTION

The present invention relates to a photocuring resin composition for orthodontics which is suitable for the preparation of a splint to be used in treatment of dysfunctions of tempromandibular joint in the dental remedy.

BACKGROUND OF THE INVENTION

In general, in treatment of dysfunctions of tempromandibular joint such as tempromandibular arthrosis, bruxism, and malocclusion, there has been used an orthodontic treatment in which an orthodontic appliance having a thickness of 1~3 mm and having a shape so as to cover a tooth occlusal surface, called as a splint or a bite plate, is set in the oral cavity of a patient for a certain period of time, thereby leading a mandibule to a normal position.

Usually, in the preparation of such an orthodontic appliance, acrylic resins such as dental self-curing resins or heat-curing resins are used, and these resins are applied in the following procedures.

In case where a self-curing resin is used, while using a gnathostatic model which is prepared by setting a plaster model prepared by impression taking of a dentition of a patient in an articulator, thereby reproducing the oral cavity, a self-curing resin powder is first mixed with a liquid to prepare a paste; the paste is then made in a plate-like state and formed upon light adaptation on the dentition of the gnathostatic model, followed by achieving both occlusal equilibration and adjustment of surface characterization; and after the resin has been cured, adjustment of surface characterization such as one on the marginal shape as well as polishing are achieved.

On the other hand, in case where a heat-curing resin is used, while using a gnathostatic model as prepared in the same manner as in the case of a self-curing resin, a wax model having the same type as in an orthodontic appliance is first prepared on the gnathostatic model by using a wax; the wax model is invested in a flask by using a plaster; after the resin has been cured, voids obtained after removing the wax with hot water, etc. are filled with a resin in a dough stage as prepared by mixing a heat-curing resin powder with a liquid; the resin is cured upon heating for a certain period of time; the cured resin is then excavated out from the flask; and adjustment of surface characterization as well as polishing are achieved.

As described above, since the preparation of the conventional orthodontic appliance is carried out in an indirect method using the gnathostatic model in which the oral cavity is reproduced, such is the present state that not only it takes plenty of time and labor, but also since all of these working steps must be manually carried out, there is often a scattering depending on the technician so that a fully satisfied precision is hardly obtained. Also, since rigid and brittle properties inherent in the acrylic resin are succeeded to the finished orthodontic appliance, the orthodontic appliance is generally poor in elasticity and is likely broken. In addition, although the orthodontic appliance such as a splint is usually retained in the oral cavity by utilizing a tooth undercut, in case where the undercut is designed to be large in order to have a high retention strength, the material poor in elasticity makes the orthodontic appliance readily break at the time of placement and removal. On the other hand, in case where the undercut is designed to be small, there is a drawback that the orthodontic appliance can not be thoroughly retained, whereby it is likely to drop. For these reasons, such problem is caused which requires to retain the orthodontic appliance by newly providing with a clasp, etc., and the structure of the orthodontic appliance becomes inevitably complicated so that the preparation and adjustment of the appliance are extremely difficult, whereby it takes plenty of time and labor.

SUMMARY OF THE INVENTION

Thus, an object of the present invention is to provide a resin composition for orthodontics by which not only an orthodontic appliance with a good precision can be directly prepared in the oral cavity of a patient within a short period of time without using a gnathostatic model, but also the resulting orthodontic appliance has a proper elasticity so that a thorough retention strength can be obtained by only utilizing a tooth undercut without imparting a retention structure such as a clasp.

In order to attain the above-described object, the present inventors made extensive and intensive investigations. As a result, it has been found that if a resin composition for orthodontics is of a photocuring type to prepare one paste, an orthodontic appliance with a good precision can be directly prepared in the oral cavity of a patient within a short period of time by curing the resin in the oral cavity upon irradiation with a light, without preparing a gnathostatic model; and that if a photocuring resin composition for orthodontics is compounded with a combination of a urethane bond-containing (meth)acrylate having an average molecular weight of from 300 to 5,000 and having at least one unsaturated double bond and a crosslinked polyurethane powder, not only the resulting cured material has an elasticity and can thoroughly retain an orthodontic appliance by only utilizing a tooth undercut without providing with a retention structure such as a clasp, but also the breakage of the orthodontic appliance can be prevented at the time of placement and removal.

That is, the photocuring resin composition for orthodontics according to the present invention comprises:

(a) 5~50% by weight of a urethane bond-free (meth)acrylate having an average molecular weight of 100~300 and having at least one unsaturated double bond;

(b) 10~60% by weight of a urethane bond-containing (meth)acrylate having an average molecular weight of 300~5,000 and having at least one unsaturated double bond;

(c) 5~30% by weight of a crosslinked polyurethane powder;

(d) 10~50% by weight of an inorganic filler; and (e) 0.03~3% by weight of a photocuring initiator.

In this embodiment, up to 60% by weight of the inorganic filler can be substituted with an organic-inorganic composite filler.

DETAILED DESCRIPTION OF THE INVENTION

Said component (a), i.e. "a urethane bond-free (meth)acrylate having an average molecular weight of 100~300 and having at least one unsaturated double bond", functions as a crosslinking agent in curing of the photocuring resin composition for orthodontics, increases the strength of the composition after curing and effectively acts in stabilization of physical properties of an orthodontic appliance over a long period of time, and refers to a urethane bond-free monomer or resin having an unsaturated double bond, such as unsaturated polyesters. Specific examples of the component (a) which can be used in the present invention include 2-ethylhexyl methacrylate, n-butyl methacrylate, isobutyl methacrylate, t-butyl methacrylate, alkyl methacrylate, methoxyethyl methacrylate, 2-hydroxybutyl methacrylate, benzyl methacrylate, phenyl methacrylate, phenoxyethyl methacrylate, ethylene glycol dimethacrylate, diethylene glycol dimethacrylate, triethylene glycol dimethacrylate, hydroxyethyl methacrylate, 1,3-butylene glycol dimethacrylate, 1,4-butylene glycol dimethacrylate, neopentyl glycol dimethacrylate, 1,6-hexanediol dimethacrylate, and acrylates corresponding to these methacrylates. These methacrylates or acrylates can be used singly or in admixture of two or more thereof. In case where the average molecular weight is less than 100, the monomer is readily volatile, whereas in case where it exceeds 300, the resulting cured material is brittle and poor in durability thus not proper. Also, in case where the amount of the component (a) to be compounded is less than 5% by weight, the strength of the resulting cured material is not satisfactory, whereas in case where it exceeds 50% by weight, the resulting cured material is too rigid to obtain a thorough elasticity.

Said component (b), i.e. "a urethane bond-containing (meth)acrylate having an average molecular weight of 300~5,000 and having at least one unsaturated double bond" has a function for imparting an elasticity to the cured material in combination with the component (c), i.e. "a crosslinked polyurethane powder" and refers to a urethane oligomer or resin having an unsaturated double bond. Specific examples of the component (b) which can be used in the present invention include di-2-methacryloxyethyl-2,2,4-trimethylhexamethylene dicarbamate, 1,3,5-tris[1,3-bis(methacryloyloxy)-2-propoxycarbonylaminohexane]-1,3,5-(1H, 3H, 5H)triazine-2,4,6-trione, and acrylates corresponding thereto; a urethane oligomer synthesized from 2,2'-di(4-hydroxycyclohexyl)propane, 2-oxepanone, hexamethylene diisocyanate, and 2-hydroxyethyl methacrylate or 2-hydroxyethyl acrylate; and a urethane oligomer synthesized from 1,3-butanediol, hexamethylene diisocyanate, and 2-hydroxyethyl methacrylate or 2-hydroxyethyl acrylate. These methacrylates or acrylates can be used singly or in admixture of two or more thereof. In case where the average molecular weight is less than 300, the paste likely to break down, whereas in case where it exceeds 5,000, the paste is so rigid as to not impart good workability thus not suitable. Also, in case where the amount of the component (b) to be compounded is less than 10% by weight, a strength and an elasticity required to the cured material as an orthodontic appliance are not obtained, whereas in case where it exceeds 60% by weight, the paste is so brittle that the workability is lowered.

Said component (c), i.e. "a crosslinked polyurethane powder" has an effect for decreasing an elastic modulus of the cured material by utilizing the elasticity of the polyurethane, to thereby lead to solution of such a problem that a thin portion such as en edge of the orthodontic appliance is broken at the time of placement and removal, and enables to obtain a thorough retention strength by only utilizing a tooth undercut without imparting a retention structure such as a clasp. Specific examples of component (c) which can be used in the present invention include a crosslinked polyurethane powder synthesized from 2-oxepanone 1,6-diisocyanatehexan and 2-ethyl-2-hydroxyethyl-1,3-propanediol [Trade name "Art Pearl C-400" (made by Negami Chemical Industrial Co.)]. In case where the amount of the crosslinked polyurethane powder to be compounded is less than 5% by weight, the elastic modulus of the cured material can not be thoroughly decreased, whereas in case where it exceeds 30% by weight, the resulting cured material is brittle. Also, a polyurethane powder having no crosslink is improper because the polymer is likely to swell in the monomer, leading to deterioration of the storage stability.

Said component (d), i.e. "an inorganic filler" has a function to give a strength to the cured material. Specific examples of the component (d) which can be used in the present invention include various glasses such as barium glass, alumina glass, and potassium glass; and powders such as those of silica, synthetic zeolite, calcium phosphate, feldspar, aluminum silicate, calcium silicate, magnesium carbonate, and quartz. Although those having a mean particle size of 100 $\mu$m or less are usually used, fine particles having a particle size in the order of several nanometers can also be used. It is preferred that these inorganic fillers are previously subjected to surface modified. Examples of surface-modified agents which can be used include organo-silicon compounds such as $\gamma$-methacryloxypropyl trimethoxysilane, vinyl trichlorosilane, vinyl triethoxysilane, vinyl trimethoxysilane, vinyl triacetoxysilane, and vinyl tri(methoxyethoxy)silane, and the surface-modified is carried out in the known silane-modified method. In case where the amount of the inorganic filler to be compounded is less than 10% by weight, the resulting cured material is brittle, whereas in case where it exceeds 50% by weight, the composition paste is excessively rigid so that the workability tends to be lowered. In addition, in the photocuring resin composition for orthodontics according to the present invention, for the purpose of depressing the polymerization shrinkage at the time of curing, it is possible to substitute a part of the inorganic filler with an organic-inorganic composite filler. In this case, however, since the strength is lowered, it is necessary that the amount of the organic-inorganic composite filler to be compounded up to 60% by weight of the whole of the filler. As the organic-inorganic composite filler, an organic-inorganic composite filler as obtained by mixing the above-described inorganic filler with a monomer, curing the mixture, and then grinding the cured mixture can be used.

The component (e), i.e. "a photocuring initiator" a photocuring initiator comprising a combination of a sensitizing agent capable of polymerizing a photocuring resin composition for orthodontics by the action of a visible light ray of from 390 to 830 nm with a reducing agent can be used.

Specific examples of the sensitizing agent which can be used in the present invention include camphorquinone, benzil, diacetyl, benzyl dimethyl ketal, benzyl diethyl ketal, benzyl di(2-methoxyethyl) ketal, 4,4'-dimethylbenzyl-dimethylketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanethone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10, 10-dioxide, thioxanthone-10-oxide, benzoin methyl ether, benzoin ethyl ether, isopropyl ether, benzoin isobutyl ether, benzophenone, bis(4-dimethylaminophenyl) ketone, 4,4'-bisethylamino benzophenone, acyl phosphine oxides such as (2,4,6-trimethylbenzoyl)diphenylphosphine oxide, and azido group-containing compounds. These sensitizing agents can be used singly or in admixture of two or more thereof.

Also, as the reducing agent, tertiary amines and the like are generally used. Specific examples of tertiary amines which can be used in the present invention include N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. Examples of other reducing agents which can be used in the present invention include benzoyl peroxide, sodium sulfinate derivatives, and organometallic compounds. These reducing agents can be used singly or in admixture of two or more thereof.

In addition, in case where the amount of the photocuring initiator to be compounded is less than 0.03% by weight, a thorough photocuring effect can not be obtained, whereas in case where it exceeds 3% by weight, the curing is initiated before the irradiation with a light, and hence, such is improper.

The photocuring resin composition for orthodontics according to the present invention can be added with the known polymerization inhibitors, ultraviolet light absorbers, plasticizers, pigments, perfume, antioxidants, anti-fungus agents, surfactants, and the like, if desired.

The photocuring resin composition for orthodontics according to the present invention comprising the components as described above is characterized in that the resulting cured material has a proper elasticity. Specifically, if the cured material has an elastic modulus, as measured by the three-point bending test, of 0.2~1.5 GPa and an elastic strain of 10~30%, it has been confirmed from the clinical viewpoint that even when a load is produced in an edge or thin portion of the orthodontic appliance, the cure material is hardly broken.

In addition, although the photocuring resin composition for orthodontics according to the present invention is in a paste-like state at the time of compounding, it is provided in a sheet-like state having a proper plasticity after extrusion molding in a predetermined thickness. Actually, in case where a splint is prepared, the photocuring resin composition for orthodontics in a sheet-like state is applied on a maxillary dentition of a patient; adaptation and trimming are carried out, thereby adjusting the preliminary shape to a splint form; a mandibule is then lightly occluded, and adjustment of the surface characterization and adjustment to the occlusion relation are further carried out; thereafter, a light is irradiated in the oral cavity by using a hand-type dental light irradiating apparatus for photocuring for several minutes, thereby achieving primary polymerization; and finally, the orthodontic appliance after the primary polymerization is taken out from the maxilla and subjected to complete polymerization by using a dental light irradiating apparatus for photocuring to completely cure it, and final forming of the surface characterization and polishing are carried out, thereby completing a splint. Since this method is a method for directly preparing an orthodontic appliance in the oral cavity of a patient without using gnathostatic models, an orthodontic appliance with a good precision can be prepared within a short period of time. Also, since the thus obtained splint has an elasticity, a thorough retention strength can be obtained by only utilizing a tooth undercut without imparting a retention structure such as a clasp. Also, since this elasticity is retained over a long period of time, such splint has effects that not only the placement and removal are easy, but also no breakage occurs at the time of placement and removal.

The present invention is described in more detail with reference to the following Examples, but it should not be construed that the present invention is limited thereto.

EXAMPLE 1

Component (a):

| | |
|---|---|
| 1,3-Butylene glycol dimethacrylate (average molecular weight: 226): | 8.3 wt % |

Component (b):

| | |
|---|---|
| Di-2-methacryloxyethyl-2,2,4-trimethylhexamethylene dicarbamate (average molecular weight: 471): | 8.3 wt % |
| Urethane oligomer (average molecular weight: 1,508): | 31.6 wt % |

Trade name "NK Oligo U-108" (made by Shin-Nakamura Chemical Co.), which is a urethane oligomer synthesized from 2,2'-di(4-hydroxycyclohexyl)propane, 2-oxepanone, hexamethylene diisocyanate, and 2-hydroxyethyl methacrylate Component (c)

| | |
|---|---|
| Crosslinked polyurethane powder (mean particle size: 14 μm): | 20.0 Wt % |

Trade name "Art Pearl C-400" (made by Negami Chemical Industrial Co.)

Component (d)

| | |
|---|---|
| Ultrafine silica (mean particle size: 0.016 μm): | 20.0 wt % |

Trade name "R-972" (made by Nippon Aerozil Co.)

| | |
|---|---|
| Organic-inorganic composite powder (mean particle size: 50 μm): | 10.0 wt % |

A powder obtained by heat curing a mixture comprising 80% by weight of trimethylolpropane trimethacrylate, 1% by weight of azoisobutyronitrile, and 19% by weight of a ultrafine silica powder (mean particle size: 0.016 μm) and grinding the cured material Component (e)

| | |
|---|---|
| Camphorquinone: | 0.6 wt % |
| Ethyl 4-dimethylaminobenzoate: | 0.6 wt % |
| Polymerization inhibitor: | |
| Di-t-butylhydroxytoluene | 0.6 wt % |

The respective components were weighed, and then mixed and kneaded with each other to obtain a photocuring resin composition for orthodontics.

This composition was filled in a mold having a size of 2 mm×2 mm×25 mm, adapted on a glass sheet via a cellophane paper, and then cured upon irradiation with a visible light ray for 5 minutes in the upper direction in one side thereof by means of a dental light irradiating apparatus for photocuring (LABOLIGHT LV-II, manufactured by GC Corporation). The thus obtained specimen was dipped in distilled water at 37° C. for 24 hours and subjected to a three-point bending test under conditions of a span of 20 mm and a crosshead speed of 1 mm/min by means of a autograph (manufactured by Shimadzu Corporation). As a result, the specimen had a bending strength of 28 MPa, a elastic modulus of 0.5 GPa, and an elastic strain of 23%.

Next, this composition was made in a sheet-like form having a thickness of 3 mm, a length of 130 mm, and a width of 20 mm, and a splint was prepared therefrom in the following manner. That is, a maxillary dentition of a patient was thoroughly dried with air; the thus formed sheet was adapted on the dried dentition, thereby adjusting the preliminary shape to a splint form; a mandibule was then lightly occluded, and adjustment of the surface characterization and adjustment to the occlusion relation were further carried out; and thereafter, a light was irradiated by using a hand-type dental visible light irradiating apparatus for photocuring (GC NEW LIGHT VL-II, manufactured by GC Corporation) for several minutes, thereby achieving primary polymerization. The orthodontic appliance after the primary polymerization was taken out from the oral cavity and again irradiated with a visible light for 5 minutes by using a dental light irradiating apparatus for photocuring (LABOLIGHT LV-II, manufactured by GC Corporation) to achieve complete polymerization; and final forming of the surface characterization and polishing were carried out, thereby completing a splint. It took about 40 minutes to complete the preparation. When the resulting splint was set in the oral cavity of a patient, it had a good fitness and a proper elasticity and was thoroughly retained only by means of an undercut. Also, when the placement and removal were repeated, any breakage of the splint was not observed.

EXAMPLE 2

Component (a)

| | |
|---|---|
| Triethylene glycol dimethacrylate (average molecular weight: 286): | 8.3 wt % |

Component (b)

| | |
|---|---|
| Di-2-methacryloxyethyl-2,2,4-trimethylhexamethylene dicarbamate (average molecular weight: 471): | 31.6 wt % |
| Urethane oligomer (average molecular weight: 686): | 8.3 wt % |

Trade name "Art Resin SH-101" (made by Negami Chemical Industrial Co.), which is a urethane oligomer synthesized from 1,3-butanediol, hexamethylene diisocyanate, and 2-hydroxyethyl methacrylate Component (c)

| | |
|---|---|
| Crosslinked polyurethane powder (mean particle size: 14 μm): | 20.0 wt % |

Trade name "Art Pearl C-400" (made by Negami Chemical Industrial Co.)

Component (d)

| | |
|---|---|
| Ultrafine silica (mean particle size: 0.016 μm): | 30.0 wt % |

Trade name "R-972" (made by Nippon Aerozil Co.)

Component (e)

| | |
|---|---|
| Camphorquinone: | 0.6 wt % |
| Ethyl 4-dimethylaminobenzoate: | 0.6 wt % |
| Polymerization inhibitor: | |
| Di-t-butylhydroxytoluene: | 0.6 wt % |

The respective components were weighed, and then mixed and kneaded with each other to obtain a photocuring resin composition for orthodontics.

A three-point bending test was carried out in the same manner as in Example 1. As a result, the bending strength was 25 MPa., the elastic modulus was 0.6 GPa, and the elastic strain was 17.3%. Also, a splint was prepared in the same manner as in Example 1. It took about 40 minutes to complete the preparation, and a splint having a superior fitting precision, a proper elasticity, and a thorough retention strength only by means of an undercut was obtained within a short period of time.

EXAMPLE 3

Component (a)

| | |
|---|---|
| 1,3-Butylene glycol dimethacrylate (average molecular weight: 226): | 8.3 wt % |

Component (b)

| | |
|---|---|
| Di-2-methacryloxyethyl-2,2,4-trimethylhexamethylene dicarbamate (average molecular weight: 471) | 8.3 wt % |
| Urethane oligomer (average molecular weight: 1,508): | 31.6 wt % |

Trade name "NK Oligo U-108" (made by Shin-Nakamura Chemical Co.), which is a urethane oligomer synthesized from 2,2'-di(4-hydroxycyclohexyl)propane, 2-oxepanone, hexamethylene diisocyanate, and 2-hydroxyethyl methacrylate Component (c)

| | |
|---|---|
| Crosslinked polyurethane powder (mean particle size: 14 μm): | 7.0 wt % |

Trade name "Art Pearl C-400" (made by Negami Chemical Industrial Co.)

Component (d)

| | |
|---|---|
| Ultrafine silica (mean particle size: 0.016 μm): [Trade name "R-972" (made by Nippon Aerozil Co.)] | 28.0 wt % |
| Organic-inorganic composite powder (mean particle size: 50 μm): | 15.0 wt % |

A powder obtained by heat curing a mixture comprising 40% by weight of a mixed solution containing di-2-methacryloxy-2,2,4-trimethylhexamethylene dicarbmate and triethylene glycol dimethacrylate (weight ratio=1:1) and 1% azoisobutyronitrile, and 60% by weight of a fine silica powder (mean particle size: 0.5 μm) and grinding the cured material Component (e)

| | |
|---|---|
| Camphorquinone: | 0.6 wt % |
| Ethyl 4-dimethylaminobenzoate: | 0.6 wt % |
| Polymerization inhibitor: | |
| Di-t-butylhydroxytoluene: 0.6 wt % | |

The respective components were weighed, and then mixed and kneaded with each other to obtain a photocuring resin composition for orthodontics.

A three-point bending test was carried out in the same manner as in Example 1. As a result, the bending strength was 48 MPa., the elastic modulus was 1.2 GPa, and the elastic strain was 12.3%. Also, a splint was prepared in the same manner as in Example 1. It took about 40 minutes to complete the preparation, and a splint having a superior fitting precision, a proper elasticity, and a thorough retention strength only by means of an undercut was obtained within a short period of time.

EXAMPLE 4

Component (a):

| | |
|---|---|
| Ethylene glycol dimethacrylate (average molecular weight: 198): | 8.3 wt % |

Component (b):

| | |
|---|---|
| Di-2-methacryloxyethyl-2,2,4-trimethylhexamethylene dicarbamate (average molecular weight: 471): | 8.3 wt % |
| Urethane oligomer (average molecular weight: 1,508): | 31.6 wt % |

Trade name "NK Oligo U-108" (made by Shin-Nakamura Chemical Co.), which is a urethane oligomer synthesized from 2,2'-di(4-hydroxycyclohexyl)propane, 2-oxepanone, hexamethylene diisocyanate, and 2-hydroxyethyl methacrylate Component (c)

| | |
|---|---|
| Crosslinked polyurethane powder (mean particle size: 14 μm): | 27.0 wt % |

Trade name "Art Pearl C-400" (made by Negami Chemical Industrial Co.)

Component (d)

| | |
|---|---|
| Ultrafine silica (mean particle size: 0.016 μm): | 23.0 wt % |

Trade name "R-972" (made by Nippon Aerozil Co.)

Component (e)

| | |
|---|---|
| Camphorquinone: | 0.6 wt % |
| Ethyl 4-dimethylaminobenzoate: | 0.6 wt % |
| Polymerization inhibitor: | |
| Di-t-butylhydroxytoluene: | 0.6 wt % |

The respective components were weighed, and then mixed and kneaded with each other to obtain a photocuring resin composition for orthodontics.

A three-point bending test was carried out in the same manner as in Example 1. As a result, the bending strength was 21 MPa., the elastic modulus was 0.3 GPa, and the elastic strain was 24%. Also, a splint was prepared in the same manner as in Example 1. It took about 40 minutes to complete the preparation, and a splint having a superior fitting precision, a proper elasticity, and a thorough retention strength only by means of an undercut was obtained within a short period of time.

EXAMPLE 5

Component (a)

| | |
|---|---|
| 1,3-Butylene glycol dimethacrylate (average molecular weight: 226): | 20.0 wt % |

Component (b)

| | |
|---|---|
| 1,3,5-Tris[1, 3-bis(methacryloyloxy)-2-propoxycarbonylaminohexane]-1,3,5-(1H, 3H, 5H)triazine-2,4,6-trione (average molecular weight: 1,228): | 8.2 wt % |
| Urethane oligomer (average molecular weight: 686) | 20.0 wt % |

Trade name "Art Resin SH-101" (made by Negami Chemical Industrial Co.), which is a urethane oligomer synthesized from 1,3-butanediol, hexamethylene diisocyanate, and 2-hydroxyethyl methacrylate Component (c)

| | |
|---|---|
| Crosslinked polyurethane powder having a crosslink (mean particle size: 14 μm): | 20.0 wt % |

Trade name "Art Pearl C-400" (made by Negami Chemical Industrial Co.)

Component (d)

| | |
|---|---|
| One obtained by adding and treating powdered silica (mean particle size: 4 μm) | 30.0 wt % | a trade name "Crystalite VX-S" (made by Tatsumori Co.) with 4 parts by weight of γ-methacryloxypropyl trimethoxysilane Component (e)

| | |
|---|---|
| Camphorquinone: | 0.6 wt % |
| Ethyl 4-dimethylaminobenzoate: | 0.6 wt % |
| Polymerization inhibitor: | |
| Di-t-butylhydroxytoluene: | 0.6 wt % |

The respective components were weighed, and then mixed and kneaded with each other to obtain a photocuring resin composition for orthodontics.

A three-point bending test was carried out in the same manner as in Example 1. As a result, the bending strength was 36 mPa., the elastic modulus was 0.8 GPa, and the elastic strain was 15.3%. Also, a splint was prepared in the same manner as in Example 1. It took about 40 minutes to complete the preparation, and a splint having a superior fitting precision, a proper elasticity, and a thorough retention strength only by means of an undercut was obtained within a short period of time.

COMPARATIVE EXAMPLE 1
Component (a)

| | |
|---|---|
| 1,3-Butylene glycol dimethacrylate (average molecular weight: 226): | 8.3 wt % |

Component (b)

| | |
|---|---|
| Di-2-methacryloxyethyl-2,2,4-trimethylhexamethylene dicarbamate (average molecular weight: 471): | 8.3 wt % |
| Urethane oligomer (average molecular weight: 1,508): | 31.6 wt % |

Trade name "NK Oligo U-108" (made by Shin-Nakamura Chemical Co.), which is a urethane oligomer synthesized from 2,2'-di(4-hydroxycyclohexyl)propane, 2-oxepanone, hexamethylene diisocyanate, and 2-hydroxyethyl methacrylate Component (c): None
Component (d)

| | |
|---|---|
| Ultrafine silica (mean particle size: 0.016 $\mu$m): | 40.0 wt % |

Trade name "R-972" (made by Nippon Aerozil Co.)

| | |
|---|---|
| Organic-inorganic composite powder (mean particle size: 50 $\mu$m): | 10.0 wt % |

A powder obtained by heat curing a mixture comprising 80% by weight of trimethylolpropane trimethacrylate, 1% by weight of azoisobutyronitrile, and 19% by weight of a ultrafine silica powder (mean particle size: 0.016 $\mu$m) and grinding the cured material Component (e)

| | |
|---|---|
| Camphorquinone: | 0.6 wt % |
| Ethyl 4-dimethylaminobenzoate: | 0.6 wt % |
| Polymerization inhibitor: | |
| Di-t-butylhydroxytoluene: | 0.6 wt % |

The respective components were weighed, and then mixed and kneaded with each other to obtain a photocuring resin composition for orthodontics.

A three-point bending test was carried out in the same manner as in Example 1. As a result, the bending strength was 79 MPa., the elastic modulus was 3.7 GPa, and the elastic strain was 1.2%. Also, a splint was prepared in the same manner as in Example 1. In taking out the splint from the oral cavity, the breakage occurred in a site coming into contact with the undercut.

COMPARATIVE EXAMPLE 2
Component (a)

| | |
|---|---|
| Hydroxyethyl methacrylate (average molecular weight: 130): | 10.0 wt % |
| Triethylene glycol dimethacrylate (average molecular weight: 286): | 8.2 wt % |

Component (b)

| | |
|---|---|
| Di-2-methacryloxyethyl-2,2,4-trimethylhexamethylene dicarbamate (average molecular weight: 471): | 30.0 wt % |

Urethane oligomer: None
Component (c): None
Component (d)

| | |
|---|---|
| One obtained by adding and treating powdered silica (mean particle size: 4 $\mu$m): | 40.0 wt % | a trade name "Crystalite VX-S" (made by Tatsumori Co.) with 4 parts by weight of $\gamma$-methacryloxypropyl trimethoxysilane Component (e)

| | |
|---|---|
| Camphorquinone: | 0.6 wt % |
| Ethyl 4-dimethylaminobenzoate: | 0.6 wt % |
| Polymerization inhibitor: | |
| Di-t-butylhydroxytoluene: | 0.6 wt % |
| Other components: | |
| Polyacrylic powder having a crosslink (mean particle size: 60 $\mu$m): | 10.0 wt % |

Trade name "Art Pearl TM-150" (made by Negami Chemical Industrial Co.)

The respective components were weighed, and then mixed and kneaded with each other to obtain a photocuring resin composition for orthodontics.

A three-point bending test was carried out in the same manner as in Example 1. As a result, the bending strength was 53 MPa., the elastic modulus was 3.4 GPa, and the elastic strain was 0.7%. Also, a splint was prepared in the same manner as in Example 1. The resulting splint was poor in elasticity and insufficient in retention and readily came out.

COMPARATIVE EXAMPLE 3

Using a commercially available acrylic thermosetting resin, "GC Acron" (made by GC Corporation), which has hitherto been used for resins for orthodontics, a specimen having a size of 2 mm×2 mm×25 mm was prepared according to the heat polymerization method as indicated in the statement of this product. Using this specimen, a three-point bending test was carried out in the same manner as in Example 1. As a result, the bending strength was 95 MPa., the elastic modulus was 2.7 GPa, and the elastic strain was 5.4%. Also, a splint was prepared in the same manner as in the preparation method for orthodontic appliances using conventional thermosetting resins. As a result, it took about 8 hours to complete the preparation, and the resulting splint had no precision and was hard in retention by means of an undercut.

COMPARATIVE EXAMPLE 4

A commercially available acrylic self-curing resin, "GC Unifast II" (made by GC Corporation), which has hitherto been used for resins for orthodontics, was charged into a mold and cured according to the method of use as indicated in the statement of this product. There was thus obtained a specimen having a size of 2 mm×2 mm×25 mm was prepared. Using this specimen, a three-point bending test was carried out in the same manner as in Example 1. As a result, the bending strength was 81 MPa., the elastic modulus was 1.9 GPa, and the elastic strain was 4.1%. Also, a splint was prepared in the same manner as in the preparation method for orthodontic appliances using conventional self-curing resins. As a result, it took about 4 hours to complete the preparation, and the resulting splint had no precision and was hard in retention by means of an undercut.

The results obtained in these Examples and Comparative Examples are summarized in Table 1.

TABLE 1

| | Three-point Bending Test | | | |
|---|---|---|---|---|
| | Bending Strength (MPa) | Elastic Modulus (GPa) | Elastic strain (%) | Precision and Retention by Undercut |
| Example 1 | 28 | 0.5 | 23.0 | Good |
| Example 2 | 25 | 0.6 | 17.3 | Good |
| Example 3 | 48 | 1.2 | 12.3 | Good |
| Example 4 | 21 | 0.3 | 24.0 | Good |
| Example 5 | 36 | 0.8 | 15.3 | Good |
| Comparative Example 1 | 79 | 3.7 | 1.2 | Bad |
| Comparative Example 2 | 53 | 3.4 | 0.7 | Bad |
| Comparative Example 3 | 95 | 2.7 | 5.4 | Bad |
| Comparative Example 4 | 81 | 1.9 | 4.1 | Bad |

As is clear from the respective Comparative Examples a described above, in Comparative Example 1 wherein the component (c), i.e., "a crosslinked polyurethane powder", is not present, the elastic modulus is high, and the breakage occurs in a site coming into contact with the undercut; in Comparative Example 2 wherein both the component (b), i.e., a urethane bond-containing urethane oligomer having an unsaturated double bond in "a urethane bond-containing (meth)acrylate having an average molecular weight of from 300 to 5,000 and having at least one unsaturated double bond", and the component (c), i.e., "a crosslinked polyurethane powder", are not present, since the cured material can not be imparted with an elasticity, the elastic modulus is high, and the retention by means of a undercut is insufficient; in Comparative Example 3, since the resin is comprised of, as major components, a liquid of methyl methacrylate having a molecular weight of 100 and a crosslink-free poly-acrylic powder having a mean particle size of about 80 μm, the elasticity is poor; and in Comparative Example 4, since the resin is comprised of a composition similar to the acrylic thermosetting resin as in Comparative Example 3, the elasticity is poor.

As is clear from the respective Examples as described above, the photocuring resin compositions for orthodontics according to the present invention are, as a result of the three-point bending test, within the range of 0.2~1.5 GPa for the elastic modulus and the range of 10~30% for the elastic strain, and the cured materials resulting therefrom have a proper elasticity, and even in case where a load is applied in an edge or thin portion of an orthodontic appliance such as a splint, they are hardly broken and can retain an orthodontic appliance by utilizing a tooth undercut without using an exclusive retention equipment such as a clasp. Also, utilizing the characteristics of photocuring resins that they are superior in simplicity and workability, there is a merit that it is possible to prepare an orthodontic appliance within a short period of time directly in the oral cavity of a patient. Thus, the present invention largely contributes to the treatment of dysfunctions of tempromandibular joint in the dental remedy.

While the invention has been described in detail and with reference to specific embodiments thereof, it will be apparent to one skilled in the art that various changes and modifications can be made therein without departing from the spirit and scope thereof.

What is claimed is:

1. A photocuring resin composition for orthodontics comprising:
   (a) 5~50% by weight of a urethane bond-free (meth) acrylate having an average molecular weight of 100~300 and having at least one unsaturated double bond;
   (b) 10~60% by weight of a urethane bond-containing (meth)acrylate having an average molecular weight of 300~5,000 and having at least one unsaturated double bond;
   (c) 5~30% by weight of a crosslinked polyurethane powder;
   (d) 10~50% by weight of an inorganic filler; and
   (e) 0.03~3% by weight of a photocuring initiator, wherein compounds (b) and (c) in combination impart elasticity to said composition when cured, wherein the crosslinked polyurethane powder is synthesized from 2-oxepanone, 1,6-diisocyanate hexane and 2-ethyl-2-hydroxyethyl-1,3-propanediol.

* * * * *